United States Patent [19]

Schunk et al.

[11] 4,154,087

[45] May 15, 1979

[54] MICRORHEOSCOPIC DETECTOR FOR GASES

[75] Inventors: Günter Schunk; Albert Randow, both of Bruchköbel, Fed. Rep. of Germany

[73] Assignee: Leybold-Heraeus GmbH & Co. KG, Cologne, Fed. Rep. of Germany

[21] Appl. No.: 860,477

[22] Filed: Dec. 14, 1977

[30] Foreign Application Priority Data

Dec. 14, 1976 [DE] Fed. Rep. of Germany ....... 2656487

[51] Int. Cl.$^2$ .................. G01N 21/36; G01P 5/12
[52] U.S. Cl. .................... 73/27 R; 73/204; 73/190 EW
[58] Field of Search ............ 73/27 R, 189, 190 EW, 73/204; 318/295, 315, 319, 320; 250/250, 352

[56] References Cited

U.S. PATENT DOCUMENTS

| 3,621,707 | 11/1971 | Kolloff et al. ................ 73/27 R |
| 4,024,761 | 5/1977 | Djorup ......................... 73/204 |

*Primary Examiner*—James J. Gill
*Attorney, Agent, or Firm*—Sprung, Felfe, Horn, Lynch & Kramer

[57] ABSTRACT

A microrheoscopic detector for gases, especially for infrared gas analyzers comprises a base and a heating conductor mounted to the base. Two resistance thermometers are disposed in the area of influence of the heating conductor and comprise thin wire which is held between thicker connecting wires which are in turn affixed to the heating conductor.

8 Claims, 3 Drawing Figures

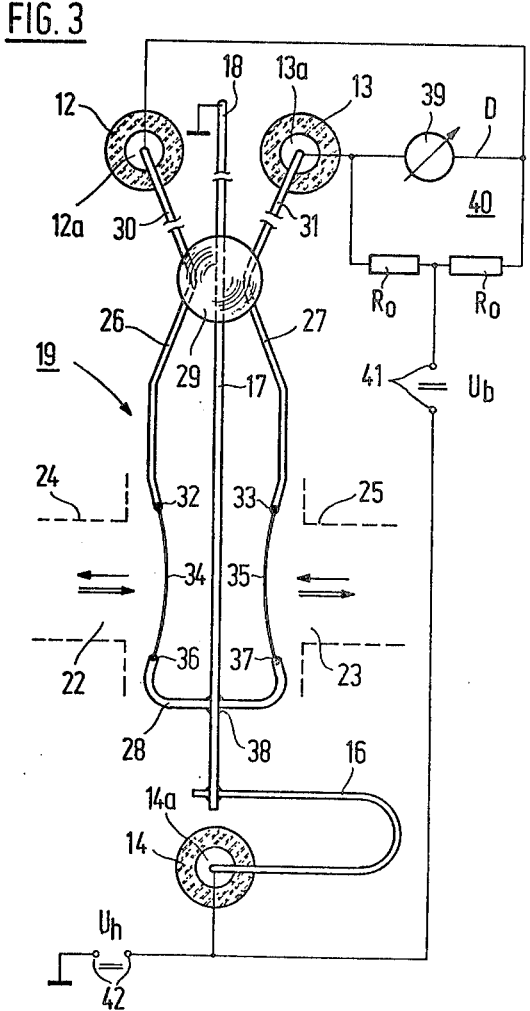

MICRORHEOSCOPIC DETECTOR FOR GASES

BACKGROUND OF THE INVENTION

The invention relates to a microrheoscopic detector for gases, especially for infrared gas analysis apparatus, comprising a heater wire and two resistance thermometers, which are disposed in the area of influence of the heater wire, and which consist of thin wire and are held between two thicker connecting wires.

In a number of physical measuring processes, it is necessary to measure very small pulsating pressures or flows of very low volume in gases. Such processes include, for example, infrared gas analysis, leakage measurements in low sensitivity ranges, breathing measurements in medicine, and other measurements involving processes in which very small amounts of gas are consumed.

For the measurement of the rate of flow of gases, microrheoscopic detectors of the kind initially described can be used which are also known as hot wire anemometers. High speed microrheoscopic detectors for gases are defined as a means of measuring the flow of very small volumes, the functioning elements of which are constituted by two or more, partially low-mass solid structures which are temperature-coupled through a gaseous path; by means of a heated solid body, which can be a relatively inert, massive part, a hot cloud is formed in the gas to be measured, and can be described by a pattern of isotherms. A forced flow deforms this gas cloud or the isotherm pattern. By means of one or more low-mass temperature sensors disposed within the gas cloud, a signal can be produced which is proportional, within limits, to the flow.

The requirement of low mass inertia in the temperature sensor results, for example, in resistance thermometers having extremely thin resistance wires whose diameter is between about 0.5 and $5 \times 10^{-3}$ mm. A low mass inertia is necessary in order that the resistance thermometers may have a sufficient resolving power in the order of magnitude between about 10 and 50 Hz.

In a rheoscopic detector for very small flows, care must also be taken to see that no free convection can take place within the sensor, which would be contrary to the forced convection of the measuring effect. This requires that the size of the active sensor volume be on the order of approximately 1 mm$^3$ and less. The length of the resistance thermometer in this case is to be between 0.4 and 1.5 mm. From the above-stated requirements and design standards it is apparent that a microrheoscopic detector of this kind is a product of delicate manufacturing technology involving stringent precision requirements. This necessarily entails high manufacturing expense involving considerable labor costs.

A microrheoscopic detector of the kind described in the beginning has become known through the dissertation presented by Günter Schunck entitled, "Schnelle Messfühler für kleine Gasströme," on Dec. 9, 1974, at the Electrical Engineering faculty of the University of Karlsruhe. In the known microrheoscopic detector, the heating conductors and the two resistance thermometers are suspended independently of one another on wire leads which permit thermal expansion on the basis of their resilient construction. While a microrheoscopic detector of this kind completely satisfies the technical requirements, experience has shown that it is sensitive to vibration and is expensive to manufacture. The vibrations which are inevitable in many measuring instruments, at times result in the destruction of the delicate resistance thermometers. Problems are also encountered in assembly, since the resistance thermometers have to be fastened individually to fusion-embedded wire leads, without placing any mechanical strain on them.

SUMMARY OF THE INVENTION

The invention is addressed to the problem of devising a microrheoscopic detector of the initially described kind, which will be substantially less sensitive to vibration and can be made with less expense as well as less waste due to rejects.

The solution of this problem is accomplished in the microrheoscopic detector described in the beginning by the fact that, in accordance with the invention, the wire leads for the resistance thermometers are affixed to the heating conductor. The supporting element for the resistance thermometers is thus the very stable heating conductor, which usually consists of platinum and has a diameter between about 15 and $30 \times 10^{-3}$ mm. This heating conductor is suspended resiliently at at least one end, but preferably at both ends, so that any vibrations are absorbed resiliently. The fixation of the wire leads to the heating conductor brings about expansion in the same direction under the influence of the alternate-side heating, so that the mechanical stress on the delicate resistance thermometers is negligible. Production becomes substantially simpler due to the fact that the fine resistance thermometers are first affixed to the heating conductor, i.e., to the wire leads attached to the heating conductor, before the entire system is fastened to a base plate or the like.

In accordance with a further embodiment it is especially advantageous if the wire lead disposed between the resistance thermometers is electroconductively connected to the heating conductor, and if the two other wire leads are affixed to the heating conductor by means of an insulator. Thus the heating conductor serves simultaneously as one of the terminal points for the measuring voltage, so that one terminal or lead-through can be dispensed with.

An especially simple embodiment is achieved if the insulating body is a glass bead into which the heating conductor and two of the connecting leads have been fused.

With regard to the mechanical stresses in resistance thermometers which are to be attributed to differences in thermal expansion in the system, special advantages are obtained if the resistance thermometers are of arcuate shape and the connecting leads meet them tangentially at their extremities. By such a construction, whose geometry will be further explained in the drawings, the corresponding bends in the connecting wires in conjunction with the curvature of the resistance thermometers whose deflection is preselected, bring about the result that the thermometer wires reliably receive a definite spatial fixation.

BRIEF DESCRIPTION OF THE DRAWINGS

An embodiment of the invention and details thereof will be explained hereinbelow with the aid of the drawings wherein:

FIG. 3 is an enlarged detail of FIG. 1, additionally showing how it is associated with a schematically represented measuring circuit in the form of a bridge circuit.

DETAILED DESCRIPTION OF THE INVENTION

Figure 1:
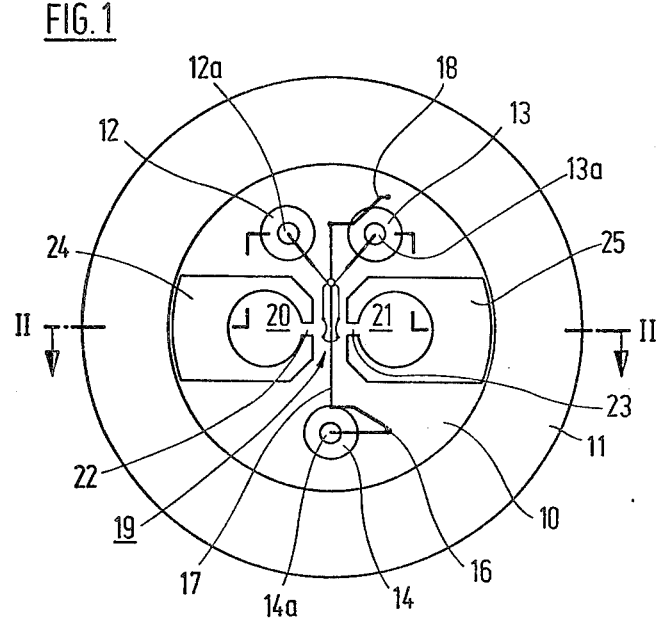
FIG. 1 is a top plan view of a microrheoscopic detector which is installed in a measuring system for an infrared gas analysis instrument.
Figure 2:
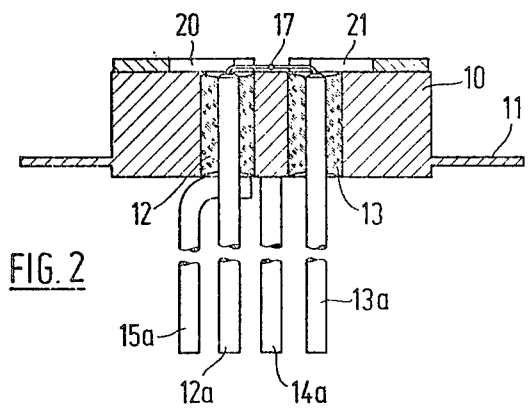
FIG. 2 is a cross section taken along line II—II of FIG. 1.

In FIGS. 1 and 2 there is shown a base plate 10 which is surrounded by a mounting flange 11. Three lead-through insulators 12, 13 and 14 are provided in the base plate, only two of them being visible in FIG. 2. In the lead-through insulators are the connecting pins 12a, 13a and 14a for the supply of the heating current and the pickup of the measuring voltage which will be further explained in conjunction with FIG. 3. An additional connecting pin 15a serves for grounding, and is connected to the base plate 10 in an electrically conducting manner.

By means of a spring loop 16 consisting of a platinum-iridium alloy, the connecting pin 14a is connected to a heating conductor 17 whose other end is connected by a supporting wire 18 to the base plate 10 and thus to the ground.

Approximately in the center of the heating conductor 17 there is an arrangement 19 of connecting wires and resistance thermometers which will be further discussed in conjunction with FIG. 3, for greater ease of comprehension. This is mentioned at this point in order to explain that the terminal ends of the arrangement 19 are connected to the connecting pins 12a and 13a. On either side of the arrangement 19 are two chambers 20 and 21, whose discharge openings 22 and 23 are situated opposite one another and face the arrangement 19. The chambers 20 and 21 and the discharge openings 22 and 23 are formed by plane-parallel segment bodies 24 and 25 of appropriate cross section, disposed in a mirror-image relationship to one another. The arrangement illustrated in FIGS. 1 and 2 is continued upwardly in a housing (not shown) in which gas-filled larger chambers and connecting passages are disposed, which lead to the chambers 20 and 21. These larger chambers, when periodically and alternately fed with radiant energy, such as infrared radiation, for example, produce a flow pulsating back and forth between the chambers 20 and 21, the arrangement 19 being encountered by the gas flow being formed through the outlet openings 22 and 23. In FIG. 3, the same parts discussed hitherto are identified by the same reference numbers. The arrangement 19 consists of three connecting wires 26, 27 and 28, of which connecting wires 26 and 27 are shown with slight bends, and they are fused together with the heating conductor 17 in an insulator 29 made of glass. The connecting wires 26 and 27 protrude from both sides of the insulator 29 and are connected by intermediate conductors 30 and 31 to the terminal pins 12a and 13a. The opposite ends of the connecting wires 26 and 27, which are made, like the heating conductor 17, of platinum, are joined at junctions 32 and 33 to resistance thermometers 34 and 35 which have a slightly arcuate shape. The other two ends of the resistance thermometers are connected by junctions 36 and 37 to the connecting wire 28, which is bent in a U shape and electrically connected at junction 38 to the heating conductor 17.

It can be seen that the ends of the connecting wires 26, 27 and 28, which are attached or welded to the resistance thermometers 34 and 35, run at a small angle to the heating conductor 17, and that the connecting wires join the resistance thermometers 34 and 35 tangentially. This has the advantage, in addition to the effect described above, that the curvature or arcuate shape of the resistance thermometers is automatically produced when the parts are assembled by welding.

The arrangement 19, whose elements are all in one plane, form together with the heating conductor 17 and the spring loop 16 a self-supporting unit, which only has to be joined to the terminal pins 12a, 13a and 14a and to the base plate 10 for assembly.

When the microrheoscopic detector is operated, for example, in an infrared gas analyzer, a pulsating alternating flow is formed which is indicated by the single and double arrows in the discharge openings 22 and 34 in FIG. 3. These flows disturb in a definite manner the pattern of isotherms which is formed coaxially about the heating conductor 17 in the state of rest, the first resistance thermometer which they encounter becoming cooler and the second resistance thermometer becoming warmer. By this effect the preset symmetry is disturbed in a bridge circuit 40 which consists of the resistance thermometers 34 and 35, two resistances $R_O$ and a diagonal conductor D in which a voltmeter 39 calibrated to the magnitude to be measured is disposed to indicate the diagonal voltage. A bridge voltage $U_b$ is applied to the terminals 41, and a heating voltage $U_h$ for the heating conductor 17 is applied to terminals 42. The principle that the resistances $R_O$ are to be many times greater than the resistances of the resistance thermometers 34 and 35 is observed. The processing of the changes of resistance at the resistance thermometers is brought about on the basis of the circuitry not further described, which in any case, considered in itself, is the state of the art and therefore needs to be explained no further. With regard to the wire diameter it is also to be stated that the thickness of the connecting wires 26, 27 and 28 is between about 10 and $20 \times 10^{-3}$ mm, while the thickness of the resistance thermometers is between about 0.5 and $5 \times 10^{-3}$ mm, preferably about $1 \times 10^{-3}$ mm.

What is claimed is:

1. A microrheoscopic detector for gases comprising:
   a base;
   a heating conductor;
   means mounting the heating conductor to the base;
   two resistance thermometers each comprising thin wire; and
   means connected only to the ends of the thin wires for mounting the resistance thermometers in the area of influence of the heating conductor and spaced therefrom in a definite spatial fixation comprising thicker connecting wires, conductively connected to the ends of the thin wires and affixed to the heating conductor.

2. The microrheoscopic detector according to claim 1, wherein one connecting wire connects one pair of ends of the resistance thermometers and is joined electroconductively to the heating conductor and the other two connecting wires are affixed to the heating conductor by an insulator.

3. The microrheoscopic detector according to claim 2, wherein the insulator is a glass bead into which the heating conductor and said other two connecting wires are embedded by fusion.

4. The microrheoscopic detector according to claim 1, characterized in that the connecting wires and the resistance thermometers form an approximately lyre-shaped outline symmetrical about the heating conductor.

5. The microrheoscopic detector according to claim 4, wherein the resistance thermometers are arcuate in shape and joined tangentially at their ends to the connecting wires.

6. The microrheoscopic detector according to claim 1, further comprising means defining two gas chambers each having discharge openings disposed in the area of the resistance thermometers.

7. The microrheoscopic detector according to claim 1, wherein the means mounting the heating conductor comprises a supporting wire connecting one end thereof to the base, an insulator in the base and means resiliently connecting the other end of the heating conductor to the insulator in the base.

8. The microrheoscopic detector according to claim 7, wherein the resilient connecting means comprises a spring clip.

* * * * *